(12) United States Patent
Harrer et al.

(10) Patent No.: US 10,380,882 B1
(45) Date of Patent: Aug. 13, 2019

(54) RECONFIGURABLE HARDWARE PLATFORM FOR PROCESSING OF CLASSIFIER OUTPUTS

(71) Applicant: International Business Machines Corporation, Armonk, NY (US)

(72) Inventors: Stefan Harrer, Sandringham (AU); Filiz Isabell Kiral-Kornek, Melbourne (AU); Benjamin S. Mashford, Parkdale (AU); Subhrajit Roy, Maribyrnong (AU)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/021,151

(22) Filed: Jun. 28, 2018

(51) Int. Cl.
*A61B 5/00* (2006.01)
*G08B 29/18* (2006.01)
*G08B 29/26* (2006.01)

(52) U.S. Cl.
CPC .......... *G08B 29/186* (2013.01); *A61B 5/0006* (2013.01); *A61B 5/4094* (2013.01); *G08B 29/26* (2013.01)

(58) Field of Classification Search
None
See application file for complete search history.

(56) References Cited

U.S. PATENT DOCUMENTS

| | | | |
|---|---|---|---|
| 3,863,625 A | 2/1975 | Viglione et al. | |
| 5,081,297 A | 1/1992 | Lebel et al. | |
| 6,051,016 A * | 4/2000 | Mesaros | A61B 17/1355 606/202 |
| 7,532,700 B2 | 5/2009 | Gara et al. | |
| 9,643,019 B2 | 5/2017 | Higgins et al. | |
| 9,851,298 B1 * | 12/2017 | Isikman | G01N 33/00 |
| 2008/0208074 A1 | 8/2008 | Snyder et al. | |
| 2014/0247151 A1 * | 9/2014 | Proud | A61B 5/0024 340/870.02 |
| 2014/0266731 A1 * | 9/2014 | Malhotra | G06F 1/163 340/573.1 |
| 2015/0164390 A1 * | 6/2015 | Larvenz | A61B 5/14532 600/365 |
| 2016/0007910 A1 * | 1/2016 | Boss | A61B 5/02055 600/301 |
| 2016/0180692 A1 * | 6/2016 | Du | G02B 27/017 340/573.1 |
| 2016/0277661 A1 * | 9/2016 | Brav | H04N 5/23206 |

(Continued)

OTHER PUBLICATIONS

Lotte et al., "A review of classification algorithms for EEG-based brain-computer interfaces", Journal of Neural Engineering, IOP Publishing, Submitted on Mar. 6, 2007.

(Continued)

*Primary Examiner* — Fekadeselassie Girma
(74) *Attorney, Agent, or Firm* — Stephanie L. Carusillo

(57) ABSTRACT

In an approach, a processor receives classified data, wherein the classified data has been output by a second processor. A processor adjusts a count based on the classified data. A processor determines whether the count is greater than a pre-set threshold, wherein the pre-set threshold is set by a switching module of the processor. Responsive to determining that the count is greater than the pre-set threshold, the processor triggers an alarm of a pre-set alarm length, wherein the pre-set alarm length is set by the switching module of the processor.

15 Claims, 4 Drawing Sheets

(56) References Cited

U.S. PATENT DOCUMENTS

| | | | |
|---|---|---|---|
| 2016/0310049 A1* | 10/2016 | Rowe | A61B 5/1477 |
| 2016/0324487 A1* | 11/2016 | Guo | G08B 21/0269 |
| 2016/0364131 A1* | 12/2016 | Dumont | G01J 1/0271 |
| 2017/0203030 A1* | 7/2017 | Brewer | A61M 5/14244 |
| 2017/0207646 A1* | 7/2017 | Boss | H02J 7/0047 |
| 2017/0224214 A1* | 8/2017 | Saigh | A61B 5/0022 |
| 2017/0359467 A1* | 12/2017 | Norris | H04M 3/568 |
| 2018/0103859 A1* | 4/2018 | Provenzano | A61B 5/02438 |
| 2018/0132778 A1* | 5/2018 | Dugan | A61B 5/14542 |
| 2018/0317875 A1* | 11/2018 | Khayrullaev | A61B 7/04 |

OTHER PUBLICATIONS

Rast et al., The Leaky Integrate-and-Fire Neuron: A Platform for Synaptic Model Exploration on the SpiNNaker Chip, 8 pages.

Gordon Brebner, "The swappable logic unit: a paradigm for virtual hardware," In Field-Programmable Custom Computing Machines, 1997. Proceedings., The 5th Annual IEEE Symposium on, pp. 77-86. IEEE, 1997. Retrieved from Internet using: http://www.dcs.ed.ac.uk/home/gordon/fan/soft-circuitry/fccm97.ps.

Kais Gadhoumi, Jean-Marc Lina, Florian Mormann, and Jean Gotman, "Seizure prediction for therapeutic devices: a review," Journal of neuroscience methods 260 (2016): 270-282.

Pearson, et al., "Design and FPGA Implementation of an Embedded Real-Time Biologically Plausible Spiking Neural Network Processor", IAS Laboratory, 4 pages.

Gadhoumi, et al., "Seizure prediction for therapeutic devices: A review", Journal of Neuroscience Methods 260 (2016) 270-282, 13 pages.

M.J. Cook, T.J. O'Brien, et al., "Prediction of seizure likelihood with a long-term, implanted seizure advisory system in patients with drug-resistant epilepsy: a first-in-man study", The Lancet Neurology, vol. 12, No. 6, pp. 563-571, Jun. 2013.

\* cited by examiner

RECONFIGURABLE HARDWARE PLATFORM FOR PROCESSING OF CLASSIFIER OUTPUTS

BACKGROUND

The present invention relates generally to the field of wearable biomedical devices, and more particularly to a reconfigurable hardware platform for wearable biomedical devices.

Machine learning classification tries to identify to which a set of categories (or subpopulations) a new observation belongs on the basis of a training set up data containing observations whose category membership is known. Currently, classifier systems consider each classification event individually. For instance, if a classifier is analyzing health-related data that is being streamed in a continuous manner, the classifier might make one classification each second. When the classifier classifies a one-second piece, the classifier has no memory of any earlier classifications.

Co-processors are computer processors used to supplement the functions of a primary processor, such as the central processing unit (CPU). One operation that can be performed by a co-processor is signal processing and more particularly digital signal processing. Co-processors can be customized for a particular use, i.e., an Application-Specific Integrated Circuit (ASIC).

SUMMARY

Aspects of an embodiment of the present invention disclose an apparatus for a wearable biomedical device. The apparatus comprises at least one sensor configured to collect data at a pre-defined time interval; a first processor configured to classify the data; and a second processor configured to process the data output by the first processor to determine whether an alarm-worthy medical event is occurring, wherein the second processor is operably coupled to the first processor.

Aspects of an embodiment of the present invention disclose a method and computer program product for using a wearable biomedical device. A processor receives classified data, wherein the classified data has been output by a second processor. A processor adjusts a count based on the classified data. A processor determines whether the count is greater than a pre-set threshold, wherein the pre-set threshold is set by a switching module of the processor. Responsive to determining that the count is greater than the pre-set threshold, the processor triggers an alarm of a pre-set alarm length, wherein the pre-set alarm length is set by the switching module of the processor.

DETAILED DESCRIPTION

Embodiments of the present invention recognize the growing demand for wearable biomedical real-time devices for healthcare purposes. These wearable devices depend on a low-power implementation in which battery size must be minimized. One example application is an epileptic seizure prediction platform. Other possible applications might monitor and classify speech, chronic pain, and neurological/psychological states, e.g. for Parkinson's disease. In such applications, because biological data carries temporal information, output from a machine learning classifier requires further processing to obtain a "memory" of classification events. Software implementation of a co-processor (e.g., running on a central processing unit (CPU)) in a real-time device to complete this required further processing consumes an unnecessary amount of power. In comparison, a hardware system achieves significant power consumption savings by employing an application-specific integrated circuit (ASIC) hardware design. Thus, embodiments of the present invention recognize that there is a need for an approach that allows for low power consumption in a wearable device. Additionally, embodiments of the present invention recognize the need for an approach that can utilize "memories" of classification events to improve a wearable biomedical device ability to predict a specific medical event.

Embodiments of the present invention provide a hardware system designed to work alongside a machine learning classifier to provide real-time triggers for an alarm system in an environment that requires low-power consumption, such as a wearable device (e.g. a smart watch). The hardware system further provides an ASIC co-processor to process the output results from a data stream running through the machine learning classifier using temporal information of the data stream, which allows the overall system to achieve higher accuracy in predicting alarm-worthy events. In this manner, as discussed in greater detail herein, embodiments of the present invention provide a biomedical wearable device worn by a user that utilizes an ASIC co-processor to help determine whether an alarm-worthy medical event is occurring. Embodiments of the present invention further enable the co-processor to be reconfigurable by providing a switching module within the co-processor that can be switched between three different modes to determine or set parameter values for the co-processor that enables a better determination of an alarm-worthy medical event.

It should be appreciated that the term "user" may refer to, unless specified otherwise, the person wearing the wearable device or an operator of the wearable device such as a medical professional, caretaker of the person wearing the wearable device, or another person with the person wearing the wearable device.

The present invention will now be described in detail with reference to the Figures.

Figure 1:
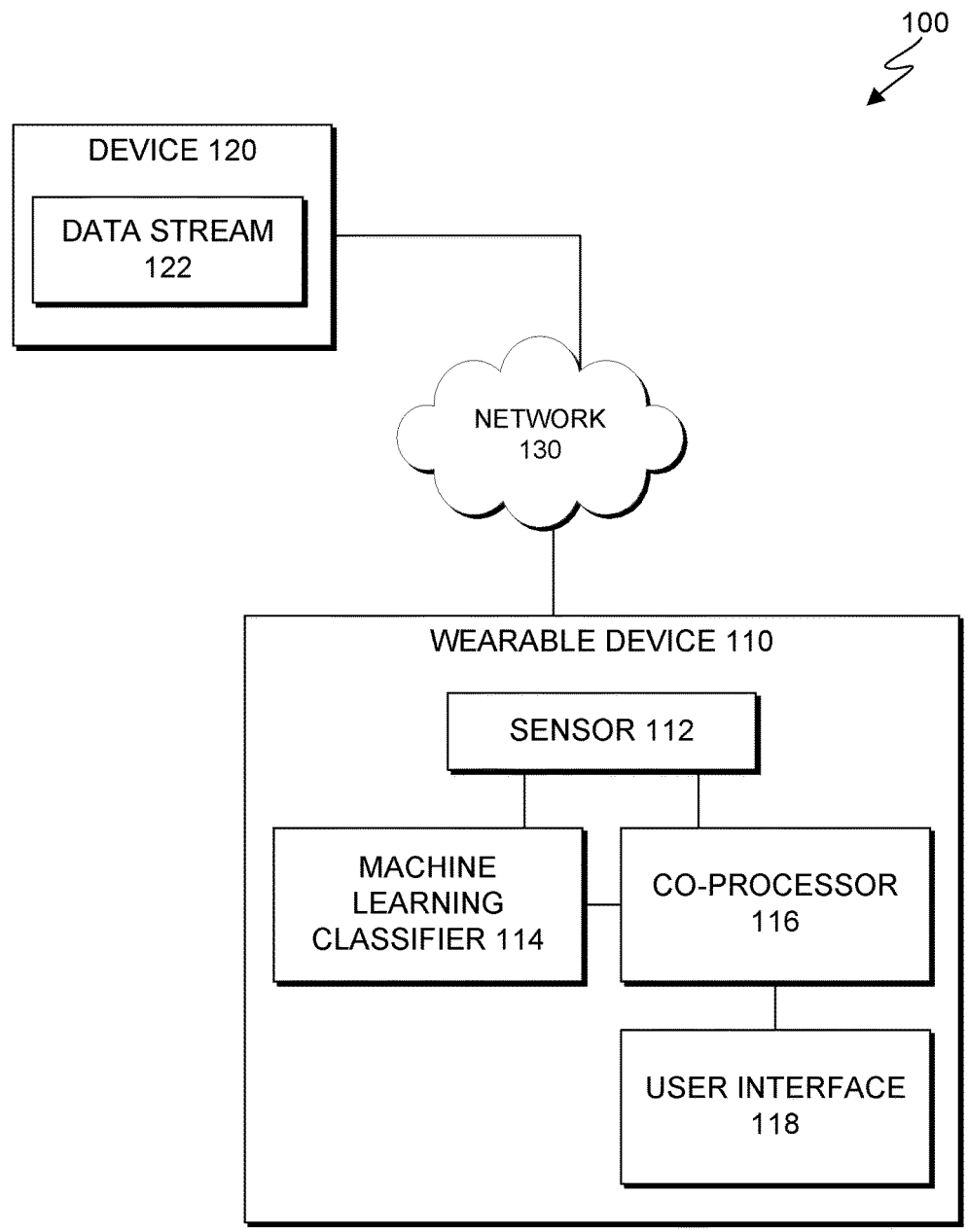
FIG. 1 depicts a functional block diagram illustrating a biomedical wearable device environment, in accordance with an embodiment of the present invention.

FIG. 1 depicts a functional block diagram illustrating biomedical wearable device environment 100, in accordance with an embodiment of the present invention. FIG. 1 provides only an illustration of one embodiment and does not imply any limitations with regard to the environments in which different embodiments may be implemented. In the depicted embodiment, biomedical wearable device environment 100 includes wearable device 110 and device 120 interconnected over network 130. Network 130 may be a local area network (LAN), a wide area network (WAN) such as the Internet, the public switched telephone network (PSTN), any combination thereof, or any combination of connections and protocols that will support communications between device 120 and wearable device 110, in accordance with embodiments of the invention. Network 130 may include wired, wireless, or fiber optic connections. Biomedical wearable device environment 100 may include additional computing devices, servers, mobile devices, sensors, or other devices not shown.

In a first embodiment, biomedical wearable device environment 100 encompasses a user (not shown) with a set of electrodes (device 120) placed on and/or within the user's scalp and wearable device 110 worn on the user's body (i.e. wrist or ankle), in which data stream 122 streams from the set of electrodes to machine learning classifier 114 of wearable device 110 to predict when the user is experiencing an epileptic seizure. In a second embodiment, biomedical wearable device environment 100 encompasses a user (not shown) wearing wearable device 110 and data stream 122 coming from sensor 112 within wearable device 110.

Device 120 operates as an outside source from which a data stream is produced or sent, such as data stream 122. In the depicted embodiment, device 120 contains data stream 122. In some embodiments, device 120 is one or more sensors, a set of electrodes, a laptop computer, tablet computer, netbook computer, personal computer (PC), a desktop computer, a smart phone, or any programmable electronic device capable of communicating with wearable device 110 via network 130. Device 120 may include components, as depicted and described in further detail with respect to FIG. 4.

Data stream 122 operates as a time-series stream of data and/or a streaming time-series data signal. In the depicted embodiment, data stream 122 comes from device 120, an outside source, but it is noted that data stream 122 can also represent any data stream coming from a sensor of wearable device 110, such as sensor 112. In a first embodiment, data stream 122 is a stream of data output by a set of electrodes, for example, an electroencephalography (EEG) signal recorded by a set of electrodes placed on and/or within a user's scalp. In this embodiment, data stream 122 output by the set of electrodes is transmitted over network 130, via wires or wirelessly, to machine learning classifier 114 of wearable device 110 to be processed. In a second embodiment, data stream 122 is a stream of data output by a sensor, such as sensor 112, of wearable device 110, for example, a data stream of accelerometry, electrodermal activity, body temperature, etc.

Wearable device 110 operates as a hardware platform that processes an incoming stream of data, such as data stream 122, to determine if a medical event is occurring and if an alarm should be triggered. In the depicted embodiment, wearable device 110 contains sensor 112, machine learning classifier 114, co-processor 116, and user interface 118. In an embodiment, wearable device 110 includes an operating system with a program for predicting alarm-worthy medical events and controls the process flow of a data stream through the components of wearable device 110. In some embodiments, wearable device 110 may be a smart watch, mobile device, or any other programmable electronic device. In some embodiments, a display of wearable device 110 is where an alert and/or notification can be displayed and viewed by a user. Wearable device 110 may include computing components as depicted and described in further detail with respect to FIG. 4.

Sensor 112 operates as sensor on wearable device 110 to detect and measure a change in a physical property relating to a user wearing wearable device 110. Sensor 112 may be a sensor that measures and collects data related to accelerometry, electrodermal activity, body temperature, etc. In an embodiment, sensor 112 refers to one sensor with capabilities to sense for more than one physical property. In another embodiment, sensor 112 refers to multiple sensors each with a capability to sense one physical property. In an embodiment, sensor 112 sends data collected to machine learning classifier 114. In an embodiment, sensor 112 sends data collected to switching module 210 of co-processor 116.

Machine learning classifier 114 operates as a computer processor configured to receive an incoming data stream and classify the data stream at a pre-defined time interval to generate an output data signal stream of positive and negative values, for example, ones (1s) and zeros (0s), respectively. In an embodiment, machine learning classifier 114 is a neural network classifier. In another embodiment, machine learning classifier 114 is a deep neural network classifier. In a first embodiment, machine learning classifier 114 receives data stream 122, which is an EEG signal recorded from a set of electrodes (not shown), and classifies data stream 122 to generate an output stream of ones (1s) and zeros (0s). In this first embodiment, machine learning classifier 114 is trained on samples of a short time interval or duration to classify between pre-seizure periods—output as a one (1)—and normal brain state—output as a zero (0). For example, machine learning classifier 114 is a neural network classifier that classifies an incoming data stream or signal every thirty seconds to classify between pre-seizure periods—ones (1s)—and normal brain state—zeros (0s). In a second embodiment, machine learning classifier 114 receives data stream 122 from a sensor, such as sensor 112, of wearable device 110 and classifies data stream 122 to generate an output stream of ones (1s) and zeros (0s).

Co-processor 116 operates as an ASIC computer processor to further process a data stream output from a machine learning classifier and determine the probability of an upcoming alarm-worthy medical event, such as an epileptic seizure. In an embodiment, co-processor 116 further processes data stream 122 output from machine learning classifier 114 to determine the probability of an upcoming alarm-worthy medical event. For example, if machine learning classifier 114 outputs multiple positive values (e.g., ones (1s)) in sequence, co-processor 116 is more likely to output a positive prediction of an alarm-worthy medical event. Co-processor 116 and its components are described in further detail with respect to FIG. 2.

User interface 118 operates as a local user interface on wearable device 110. In an embodiment, user interface 118 is a local mobile application (app) user interface on wearable device 110. In an embodiment, user interface 118 enables a user to create a local user profile on the mobile app. In an embodiment, user interface 118 enables a user to select one of three modes for selecting three parameters—step/leak-size, threshold, and alarm length—for co-processor 116. The ability to allow the user to switch between different modes makes the system re-configurable and more adaptable to different users. In an embodiment, user interface 118 enables a user to input specific values for the parameters for when the system is in a manual mode, switch between different pre-sets for when the system is in a manual mode, set rules for when to switch between different pre-sets when the system is in a rule-based mode, and/or to place the system in a machine-learning, artificial intelligence (AI) mode. The different modes for selecting the parameters for co-processor 116 are discussed in more detail below in FIG. 2. In an embodiment, user inputs and parameter modes are stored in a database (not shown) of wearable device 110 or through the mobile app off-site.

Figure 2:
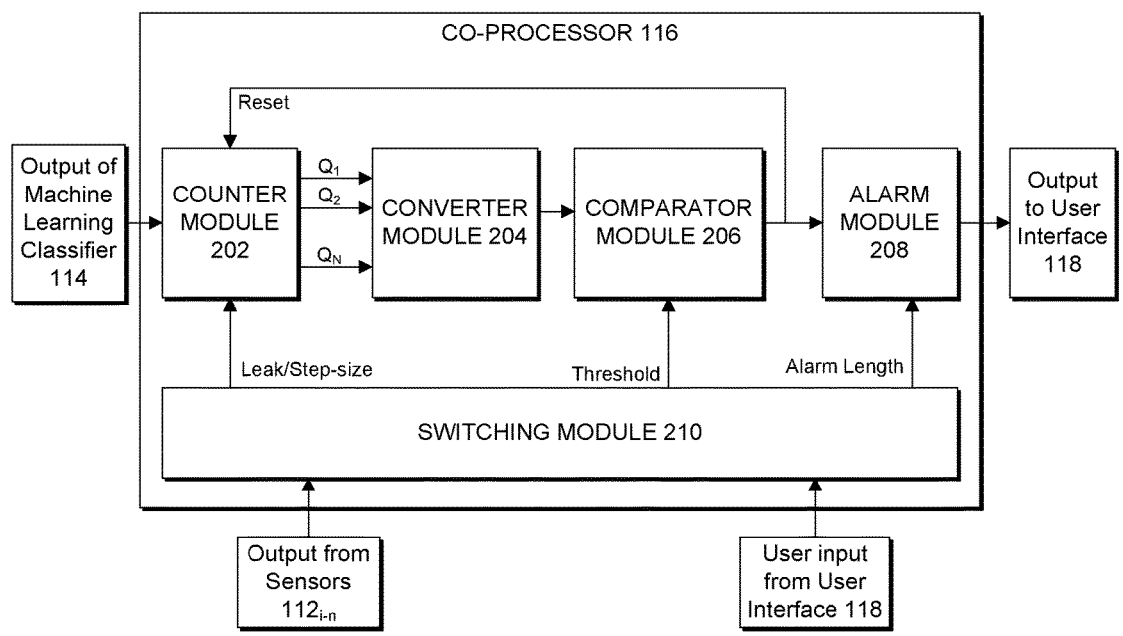
FIG. 2 depicts a functional block diagram illustrating a co-processor executing within the biomedical wearable device environment of FIG. 1, in accordance with an embodiment of the present invention.

FIG. 2 depicts a functional block diagram illustrating co-processor 116 of wearable device 110, executing within biomedical wearable device environment 100 of FIG. 1, in accordance with an embodiment of the present invention. In the depicted embodiment, co-processor 116 operates as an ASIC co-processor to further process a data stream output from a machine learning classifier and determine whether an alarm-worthy medical event is occurring, such as an epileptic seizure. In the depicted embodiment, co-processor 116 includes counter module 202, converter module 204, comparator module 206, alarm module 208, and switching module 210. It should be appreciated that the process depicted in FIG. 2 illustrates one possible arrangement of co-processor 116.

Counter module 202 operates as a special n-bit UP-DOWN counter to increment or decrement based on a data stream of ones (1s) and zeros (0s) output by a machine learning classifier according to a step-size and leak-size. In an embodiment, counter module 202 is incremented by a step-size—set by switching module 210—in response to receiving a one (1) in a data stream output by machine learning classifier 114. In an embodiment, counter module 202 is decremented by a leak-size—set by switching module 210—in response to receiving a zero (0) in a data stream output by machine learning classifier 114. In an embodiment, counter module 202 outputs streaming bits $Q_1$ to $Q_n$. In an embodiment, counter module 202 is reset in response to comparator module 206 outputting a positive prediction.

Converter module 204 operates as a digital-to-analog converter (DAC) or analog-to-digital converter to convert the streaming bits $Q_1$ to $Q_n$ from counter 202 into a digital or analog number. In an embodiment, converter module 204 is a DAC and converts the streaming bits $Q_1$ to $Q_n$ from a digital number to an analog number. In another embodiment, converter module 204 is an ADC converts the streaming bits $Q_1$ to $Q_n$ from an analog number to a digital number.

Comparator module 206 operates to compare the resulting analog or digital number from converter 204 to a threshold value. In an embodiment, comparator module 206 compares the resulting analog number to a threshold value—set by switching module 210. In another embodiment, comparator module 206 compares the resulting digital number to a threshold value—set by switching module 210. In an embodiment, comparator module 206 determines when the resulting number exceeds the threshold value. In an embodiment, once comparator module 206 determines that the resulting number exceeds the threshold value, comparator 206 module outputs a positive prediction, for example, a prediction that an epileptic seizure is occurring.

Alarm module 208 operates to trigger an alarm in response to comparator module 206 outputting a positive prediction. The alarm can be a sound, tone, and/or vibration output by a microphone (not shown) of wearable device 110. The alarm can include a message displayed on a display of wearable device 110. In an embodiment, alarm module 208 triggers an alarm of a set length of time—set by switching module 210—in response to comparator module 206 outputting a positive prediction.

Switching module 210 operates as a module for switching between three different modes of selecting three parameters—leak/step-size, threshold, and alarm length—of co-processor 116 of wearable device 110. The three modes influence the sensitivity of wearable device 110, for example, how often seizures are predicted in time and how long wearable device 110 is in an alarm-on state.

In an embodiment, switching module 210 has a manual mode, in which a user may input the three parameters manually via user interface 118. This mode enables a user to configure the system according to the user's preferences. Additionally, in manual mode, switching module 210 enables a user to switch between different pre-sets for selecting the parameter values, such as a "highly sensitive" pre-set and a "least intrusive" pre-set. The "highly sensitive" pre-set selects parameter values that cause co-processor 116 to predict alarm-worthy medical events at a higher rate, for example, when the user is driving or being generally active. The "least intrusive" pre-set selects parameters values that cause co-processor 116 to predict alarm-worthy medical events at a lower rate, for example, when the user is sleeping.

In an embodiment, switching module 210 has a logic-based or rule-based mode, in which a user may set rules for when different pre-sets should be used, e.g., a "highly sensitive" pre-set and a "least intrusive" pre-set. In several embodiments, sensors of wearable device 110 and/or outside sources of activity level information about the user are used to determine an activity level of the user. Activity levels of the user can include driving, being generally active, exercising, sleeping, etc. For example, a user can create a rule that when the user is asleep, switching module 210 is switched to the "least intrusive" pre-set. In this example, when a sensor of wearable device 110, such as an actiograph, senses that the user is asleep, switching module 210 switches to the "least intrusive" pre-set. Further in this example, once the sensor of wearable device 110 senses that the user is no longer asleep, switching module 210 switches back to the pre-set or mode for when user is awake.

In an embodiment, switching module 210 has an AI-driven mode, in which switching module 210 uses machine-learned data to learn behavioral patterns of the user. Machine-learned data includes, but is not limited to, data collected through sensors of wearable device 110 and sensors of outside sources, user input into user interface 118, and user feedback into user interface 118. For example, through machine-learned data, AI-driven mode learns to switch to the "highly sensitive" pre-set when user is being active, which can be detected through an accelerometer sensor of wearable device 110.

Figure 3:
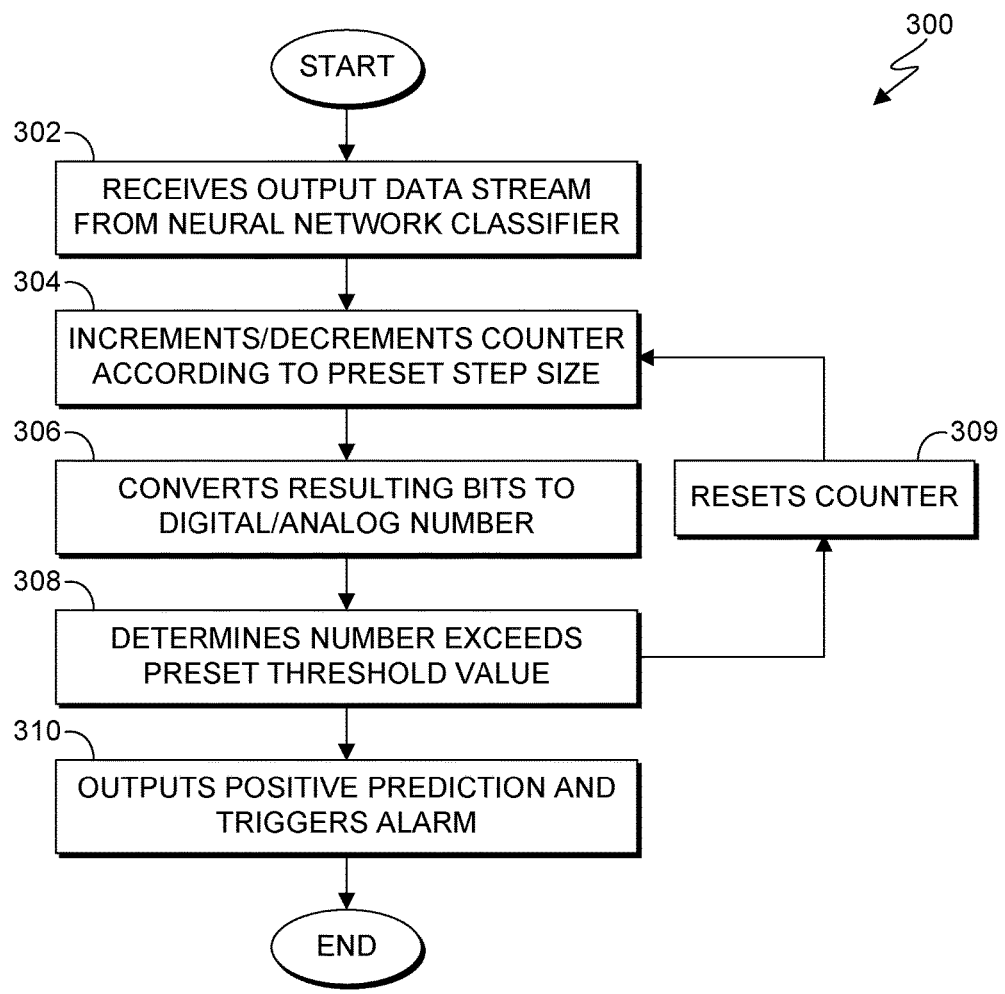
FIG. 3 depicts a flowchart of the process flow of a data stream through a co-processor, in accordance with an embodiment of the present invention.

FIG. 3 depicts a flowchart 300 of a program directing a process flow of data stream 122 through co-processor 116, in which co-processor 116 determines, based on the data stream out from machine learning classifier 114, whether an alarm should be triggered on wearable device 110, in accordance with an embodiment of the present invention. It should be appreciated that the process depicted in FIG. 3 illustrates one possible iteration of this process flow, which runs continually as data is collected and received by co-processor 116 of wearable device 110.

In step 302, co-processor 116 receives a data stream output by a machine learning classifier. In an embodiment, co-processor 116 receives at counter module 202 a data stream of ones (1s) and zeros (0s) output by machine learning classifier 114.

In step 304, counter module 202 of co-processor 116 uses discrete arithmetic to increment or decrement as the received data stream (step 302) runs through counter module 202. In an embodiment, counter module 202 is incremented or decremented according to a step-size and leak-size selected depending on the mode switching module 210 is set to. In an embodiment, counter module 202 increments by one step-size for each one (1) in the received data stream. In an embodiment, counter module 202 decrements by one leak-size for each zero (0) in the received data stream. In an embodiment, as counter module 202 increments and/or decrements based on the received data stream, counter 202 outputs digital bits $Q_1$ to $Q_n$.

In step 306, converter module 204 of co-processor 116 converts bits from counter 202 to a digital or analog number. In an embodiment, converter module 204 converts bits from counter 202 to a digital number. In another embodiment, converter module 204 converts bits from counter 202 to an analog number.

In step 308, comparator module 206 of co-processor 116 compares the digital or analog number to a threshold value selected depending on the mode switching module 210 is set to. In an embodiment, comparator module 206 compares the number to the set threshold value until the number exceeds the threshold value. In an embodiment, in response to determining the number exceeds the threshold value, comparator module 206 outputs a positive prediction and resets counter module 202.

In step 310, alarm module 208 of co-processor 116 triggers an alarm of an alarm length selected depending on the mode switching module 210 is set to. In an embodiment, alarm module 208 triggers an alarm in response to comparator module 206 outputting a positive prediction. The alarm can be a sound, tone, and/or vibration output by a microphone (not shown) of wearable device 110. In an embodiment, alarm module 208 outputs a notification or message to a display of wearable device 110 that a medical event is occurring.

Figure 4:
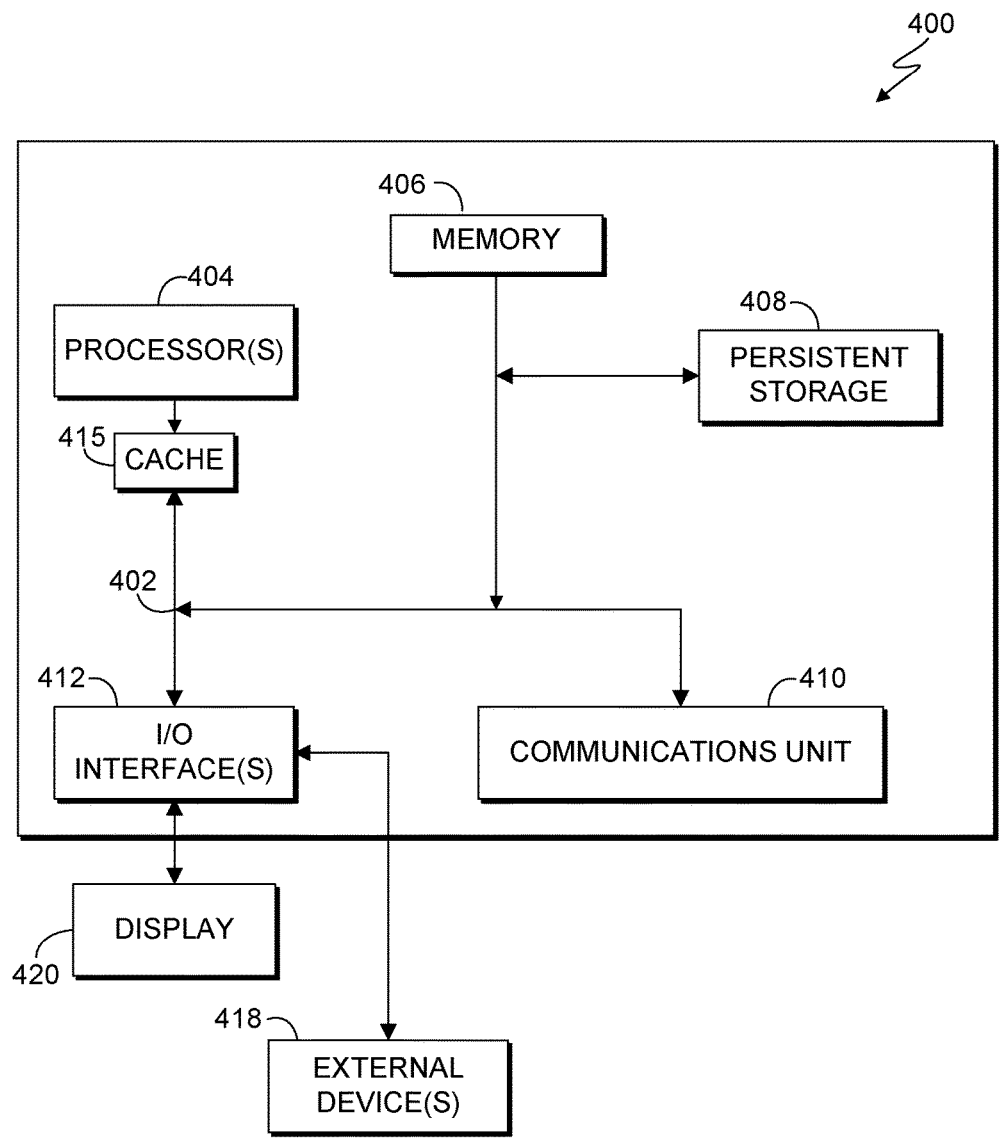
FIG. 4 depicts a block diagram of components of a computing device of biomedical wearable device environment, in accordance with an embodiment of the present invention.

FIG. 4 is a block diagram depicting components of a computer 400 suitable for wearable device 110 and device 120. FIG. 4 displays the computer 400, the one or more processor(s) 404 (including one or more computer processors), the communications fabric 402, the memory 406, the cache 416, the persistent storage 408, the communications unit 410, the I/O interfaces 412, the display 420, and the external devices 418. It should be appreciated that FIG. 4 provides only an illustration of one embodiment and does not imply any limitations with regard to the environments in which different embodiments may be implemented. Many modifications to the depicted environment may be made.

As depicted, the computer 400 operates over a communications fabric 402, which provides communications between the cache 416, the computer processor(s) 404, the memory 406, the persistent storage 408, the communications unit 410, and the input/output (I/O) interface(s) 412. The communications fabric 402 may be implemented with any architecture suitable for passing data and/or control information between the processors 404 (e.g., microprocessors, communications processors, and network processors, etc.), the memory 406, the external devices 418, and any other hardware components within a system. For example, the communications fabric 402 may be implemented with one or more buses or a crossbar switch.

The memory 406 and persistent storage 408 are computer readable storage media. In the depicted embodiment, the memory 406 includes a random access memory (RAM). In general, the memory 406 may include any suitable volatile or non-volatile implementations of one or more computer readable storage media. The cache 416 is a fast memory that enhances the performance of computer processor(s) 404 by holding recently accessed data, and data near accessed data, from memory 406.

Program instructions for computer programs may be stored in the persistent storage 408 or in memory 406, or more generally, any computer readable storage media, for execution by one or more of the respective computer processors 404 via the cache 416. The persistent storage 408 may include a magnetic hard disk drive. Alternatively, or in addition to a magnetic hard disk drive, the persistent storage 408 may include, a solid state hard disk drive, a semiconductor storage device, read-only memory (ROM), electronically erasable programmable read-only memory (EEPROM), flash memory, or any other computer readable storage media that is capable of storing program instructions or digital information.

The media used by the persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of the persistent storage 408.

The communications unit 410, in these examples, provides for communications with other data processing systems or devices. In these examples, the communications unit 410 may include one or more network interface cards. The communications unit 410 may provide communications through the use of either or both physical and wireless communications links. Computer programs may be downloaded to the persistent storage 408 through the communications unit 410. In the context of some embodiments of the present invention, the source of the various input data may be physically remote to the computer 400 such that the input data may be received and the output similarly transmitted via the communications unit 410.

The I/O interface(s) 412 allows for input and output of data with other devices that may operate in conjunction with the computer 400. For example, the I/O interface 412 may provide a connection to the external devices 418, which may include a keyboard, keypad, a touch screen, and/or some other suitable input devices. External devices 418 may also include portable computer readable storage media, for example, thumb drives, portable optical or magnetic disks, and memory cards. Software and data used to practice embodiments of the present invention may be stored on such portable computer readable storage media and may be loaded onto the persistent storage 408 via the I/O interface(s) 412. The I/O interface(s) 412 may similarly connect to a display 420. The display 420 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a wide area network (WAN), a mobile broadband network, such as a 4G and Long Term Evolution (LTE), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method comprising:
   receiving, by a counter module of a first processor of a device, classified data, wherein the classified data has been output by a second processor of the device;
   adjusting, by the counter module of the first processor of the device, a count based on the classified data, wherein adjusting the count based on the classified data comprises:
   incrementing, by the counter module of the first processor of the device, the count by a pre-set leak size based on the classified data, wherein the pre-set step-size is set by a switching module of the first processor; and
   decrementing, by the counter module of the first processor of the device, the count by the pre-set leak size based on the classified data, wherein the pre-set step-size is set by the switching module of the first processor;

determining, by a comparator module of the first processor of the device, whether the count is greater than a pre-set threshold, wherein the pre-set threshold is set by the switching module of the first processor; and responsive to determining that the count is greater than the pre-set threshold, triggering, by an alarm module of the first processor of the device, an alarm of a pre-set alarm length, wherein the pre-set alarm length is set by the switching module of the first processor.

2. The method of claim 1, further comprising:

outputting, by the counter module of the first processor of the device, the count as a digital number; and converting, by a digital-to-analog converter module of the first processor of the device, the count to an analog number.

3. The method of claim 1, wherein the switching module of the first processor of the device is configured to switch between a set of modes for selecting the pre-set step-size, the pre-set leak-size, the pre-set threshold, and the pre-set alarm length.

4. The method of claim 3, wherein the set of modes comprise a manual mode, a rule-based mode, and a machine-learning mode.

5. The method of claim 4, wherein the manual mode and the rule-based mode selects the pre-set step-size, the pre-set leak-size, the pre-set threshold, and the pre-set alarm length used by the first processor of the device based on user input through a user interface.

6. A computer program product comprising:

one or more non-transitory computer readable storage media and program instructions stored on the one or more computer readable storage media, the program instructions comprising:

program instructions to receive classified data, wherein the classified data has been output by a processor;

program instructions to adjust a count based on the classified data, wherein the program instructions to adjust the count based on the classified data comprise:

program instructions to increment the count by a pre-set leak size based on the classified data, wherein the pre-set step-size is set by a switching module of the first processor; and program instructions to decrement the count by the pre-set leak size based on the classified data, wherein the pre-set step-size is set by the switching module of the first processor;

program instructions to determine whether the count is greater than a pre-set threshold, wherein the pre-set threshold is set by a switching module; and responsive to the program instructions to determine that the count is greater than the pre-set threshold, program instructions to trigger an alarm of a pre-set alarm length, wherein the pre-set alarm length is set by the switching module.

7. The computer program product of claim 6, further comprising:

program instructions to output the count as a digital number; and program instructions to convert the count to an analog number.

8. The computer program product of claim 6, wherein the switching module is configured to switch between a set of modes for selecting the pre-set step-size, the pre-set leak-size, the pre-set threshold, and the pre-set alarm length.

9. The computer program product of claim 6, wherein the set of modes comprise a manual mode, a rule-based mode, and a machine-learning mode.

10. The computer program product of claim 6, further comprising:

program instructions to receive user input, wherein the user input comprises at least one of (1) a set of parameter values for the manual mode, (2) a set of rules for the rule-based mode, and (3) a selected mode for the switching module.

11. A computer system comprising:

one or more computer processors;

one or more non-transitory computer readable storage media;

program instructions stored on the non-transitory computer readable storage media for execution by at least one of the one or more processors, the program instructions comprising:

program instructions to receive classified data, wherein the classified data has been output by a processor;

program instructions to adjust a count based on the classified data, wherein the program instructions to adjust the count based on the classified data comprise:

program instructions to increment the count by a pre-set leak size based on the classified data, wherein the pre-set step-size is set by a switching module of the first processor; and program instructions to decrement the count by the pre-set leak size based on the classified data, wherein the pre-set step-size is set by the switching module of the first processor;

program instructions to determine whether the count is greater than a pre-set threshold, wherein the pre-set threshold is set by a switching module; and responsive to the program instructions to determine that the count is greater than the pre-set threshold, program instructions to trigger an alarm of a pre-set alarm length, wherein the pre-set alarm length is set by the switching module.

12. The computer system of claim 11, further comprising:

program instructions to output the count as a digital number; and program instructions to convert the count to an analog number.

13. The computer system of claim 11, wherein the switching module is configured to switch between a set of modes for selecting the pre-set step-size, the pre-set leak-size, the pre-set threshold, and the pre-set alarm length.

14. The computer system of claim 11, wherein the set of modes comprise a manual mode, a rule-based mode, and a machine-learning mode.

15. The computer system of claim 11, further comprising:

program instructions to receive user input, wherein the user input comprises at least one of (1) a set of parameter values for the manual mode, (2) a set of rules for the rule-based mode, and (3) a selected mode for the switching module.

* * * * *